(12) United States Patent
Fentis et al.

(10) Patent No.: US 6,712,796 B2
(45) Date of Patent: Mar. 30, 2004

(54) HIGH HYSTERESIS VALVE

(75) Inventors: Robert Fentis, Anaheim, CA (US);
Kirk Buhler, 2687 Scenic Crest La., Corona, CA (US) 92881

(73) Assignee: Kirk Buhler, Corona, CA (US)

( * ) Notice: Subject to any disclaimer, the term of this patent is extended or adjusted under 35 U.S.C. 154(b) by 298 days.

(21) Appl. No.: 09/737,896

(22) Filed: Dec. 15, 2000

(65) Prior Publication Data

US 2002/0077605 A1 Jun. 20, 2002

(51) Int. Cl.$^7$ ................................................ A61M 5/00
(52) U.S. Cl. ..................... 604/247; 604/65; 604/256; 604/323
(58) Field of Search ............................. 604/65, 66, 67, 604/93, 245–251, 253, 256, 544, 323; 251/4–10

(56) References Cited

U.S. PATENT DOCUMENTS

| | | | | |
|---|---|---|---|---|
| 4,230,102 A | * | 10/1980 | Ekbladh | 128/79 |
| 4,424,058 A | * | 1/1984 | Parsons et al. | 604/118 |
| 4,869,457 A | * | 9/1989 | Ewerlof | 251/6 |
| 5,114,412 A | | 5/1992 | Flinchbaugh | 604/247 |
| 5,429,601 A | * | 7/1995 | Conley et al. | 604/65 |
| 5,445,613 A | * | 8/1995 | Orth | 604/66 |
| 5,464,388 A | * | 11/1995 | Merte et al. | 604/153 |
| 5,522,806 A | * | 6/1996 | Schonbachler et al. | 604/250 |
| 5,681,284 A | * | 10/1997 | Herskowitz | 604/141 |
| 5,681,294 A | * | 10/1997 | Osborne et al. | 604/251 |
| 5,785,694 A | * | 7/1998 | Cohen et al. | 604/250 |
| 5,938,636 A | * | 8/1999 | Kramer et al. | 604/66 |
| 6,162,201 A | * | 12/2000 | Cohen et al. | 604/250 |
| 6,454,742 B1 | * | 9/2002 | Noecker et al. | 604/131 |

OTHER PUBLICATIONS

Marshall Brian, "How Electric Work," How Stuff Works.*

* cited by examiner

*Primary Examiner*—Weilun Lo
*Assistant Examiner*—Michael G. Bogart
(74) *Attorney, Agent, or Firm*—Kirk A. Buhler; Buhler & Associates

(57) ABSTRACT

A valve has a flow restrictor positioned outside of a lumen of a tube, which transitions between an open configuration and a closed configuration. The valve further contains a closing mechanism that automatically positions the flow restrictor to the closed configuration when a pressure in a fluid within the lumen is below a low threshold pressure, and an opening mechanism that automatically positions the first flow restrictor to the open configuration when the pressure in the fluid within the lumen is above a high threshold pressure that is higher than the low threshold pressure. The flow restrictor is preferably positioned outside the tube, although it may be positioned inside the wall of the tube, or even within the lumen of the tube. There may also be a second, downstream flow restrictor. The opening and closing mechanisms advantageously comprise a magnet or solenoid. The tube may comprise a catheter, and especially a urinary catheter. In such instances the valve stays shut long enough to provide sufficient pressure to expand the bladder, then stays open long enough to substantially drain the bladder. The process may be entirely automatic, and not dependent upon any external power source.

11 Claims, 2 Drawing Sheets

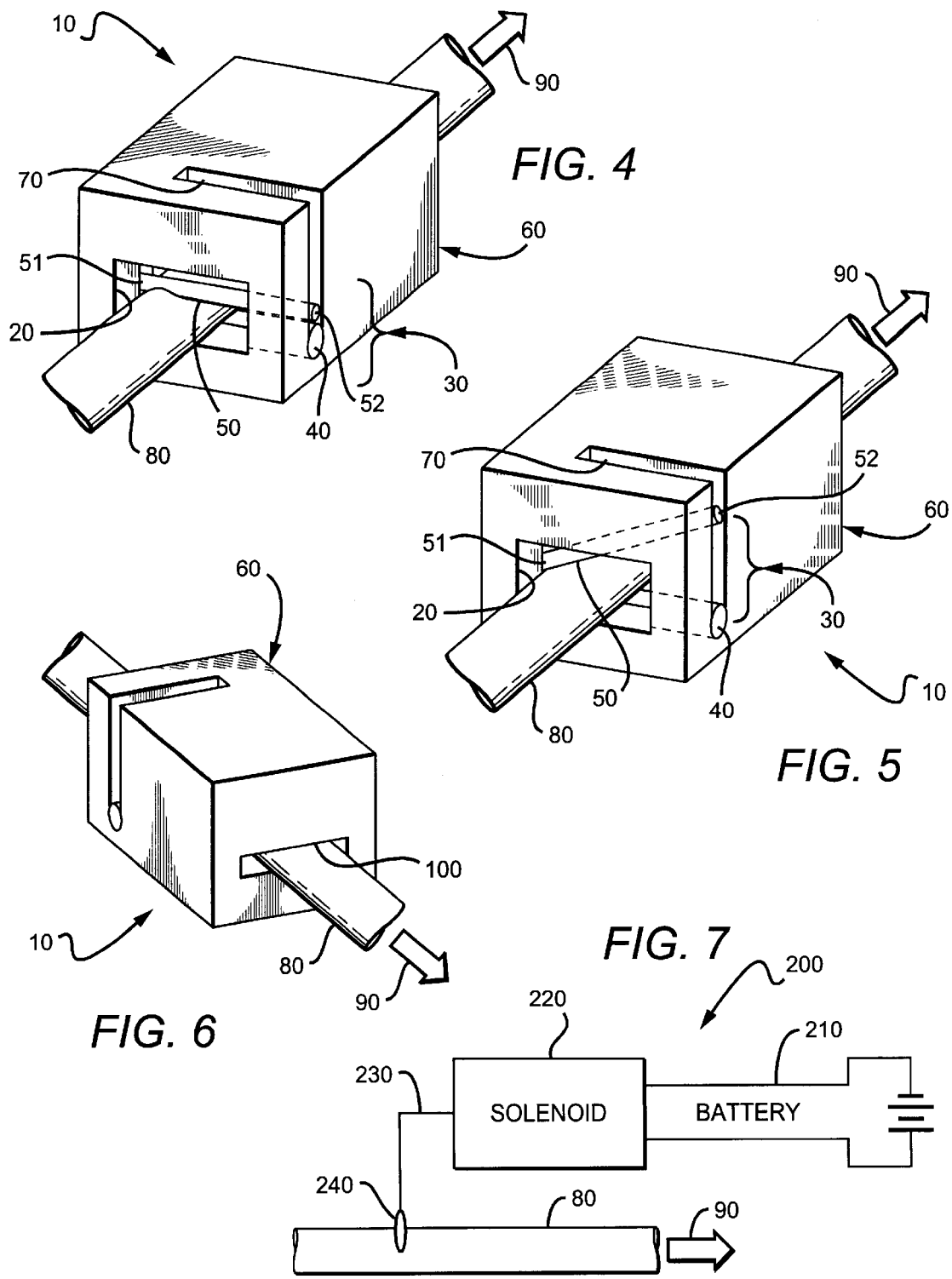

HIGH HYSTERESIS VALVE

FIELD OF THE INVENTION

The present invention relates to the field of medical catheters.

BACKGROUND OF THE INVENTION

In man and many other species urine is stored in a bladder before it is released. Urinary bladders are generally elastic to accommodate varying volumes, and tend to shrink when the bladder in not made to expand over relatively long periods of time. A significant problem exists in individuals that are catheterized for more than a few days at a time, because the catheters are often left in an open (draining) position to avoid excessive buildup of pressure. Unfortunately, leaving catheters in an open position for long periods of time greatly increases the risk of infection.

Many catheter designs have been developed to overcome these problems. A good review is set forth in U.S. Pat. No. 6,050,934 to Mikhail et al. (April 2000), which is incorporated herein by reference in its entirety. The more prevalent types of valves for use with catheters in discharging urine are those that are manually-operated. When the bladder fills with urine to the level where an individual needs to urinate, the individual opens the valve and it consequently releases the urine. The valve then shuts after release of the urine. Examples of manually-operated valves are discussed in U.S. Pat. No. 4,946,449 (August 1990) to Davis Jr.; U.S. Pat. No. 4,932,938 to Goldberg et al. (June 1990); and U.S. Pat. No. 4,846,784 to Haber (July 1989), each of which is incorporated herein by reference in its entirety.

Drawbacks generally are associated with the use of manually-operated valves in catheters. If an inadvertent, slight force is exerted to certain areas, the valve can open, thereby allowing urine to flow. For instance, force can be placed on an external valve if it is pressed between an individual's legs when the legs are crossed. If so, urine can be released and the individual can be embarrassed by the unintended failure of the catheter valve to retain the urine. Furthermore, many of the valves are difficult to operate and require much more force to operate than can be applied by some individuals. U.S. Pat. No. 6,050,934 to Mikhail et al. (April 2000) provides a manually-operated valve that reduces the amount of force required for the individual to operate, at the time that protection is needed, to help minimize inadvertent or unintended operation of the valve resulting in the unintended release of urine. However, an individual who has no feeling in the bladder region or who has no hand-control cannot operate the valve of the Mikhail '934 patent to control urine flow. In addition, manually-operated valves close unreliably under normal pressures as is generally desired, and inadequately drain small aliquots of urine from within the valve. The small aliquots of urine not drained from the valve can transmit contaminants from the outside environment and cause infection in the bladder. Yet another problem with manually operated valves is that they are not especially useful for individuals that may be unconscious, or do not have use of their hands.

Automatic valves eliminate the need for an individual to operate a valve to control urine flow. An individual who has no feeling in the bladder region or who has no hand-control can rely on an automatic valve to release urine when the bladder needs to be emptied. An example of an automatic valve can be found in U.S. Pat. No. 5,114,412 to Flinchbaugh (May 1992), the disclosure of which is incorporated herein by reference.

A drawback of many known automatic valves, however, including the valves of Flinchbaugh, is that some of the valve parts are disposed within the lumen of the catheter, and are therefore disposed in the urinary flowpath. Such valves are difficult to autoclave and therefore are problematic upon reuse. Contact with fluid may also deteriorate the valve over time. Furthermore, a valve that contacts urine in a urinary catheter can transmit contaminants from the outside environment and cause infection in the bladder.

Thus, there is a continuing need for an automatic valve that controls fluid flow in a manner that would be consistent with physiological requirements for urinary bladder expansion and contraction.

SUMMARY OF THE INVENTION

The present invention relates to devices and methods in which a valve has a flow restrictor positioned outside of a lumen of a tube, which transitions between an open configuration and a closed configuration. The valve further contains a closing mechanism that automatically positions the flow restrictor to the closed configuration when a pressure in a fluid within the lumen is below a low threshold pressure, and an opening mechanism that automatically positions the first flow restrictor to the open configuration when the pressure in the fluid within the lumen is above a high threshold pressure that is higher than the low threshold pressure.

The flow restrictor is preferably positioned outside the tube, although it may be positioned inside the wall of the tube, or even within the lumen of the tube. There may also be a second, downstream flow restrictor. The two flow restrictors may be contained in the same or in different housings.

The opening and closing mechanisms advantageously comprise a magnet, but may additionally or alternatively comprise any other suitable mechanism, including a solenoid.

A particularly advantageous class of embodiments exists where the tube comprises a catheter, and especially a urinary catheter. In such instances the valve stays shut long enough to provide sufficient pressure to expand the bladder, then stays open long enough to substantially drain the bladder. The process may be entirely automatic, and not dependent upon any external power source.

Various objects, features, aspects and advantages of the present invention will become more apparent from the following detailed description of preferred embodiments of the invention, along with the accompanying drawing in which like numerals represent like components.

BRIEF DESCRIPTION OF THE DRAWING

FIG. 4 is a perspective view of a valve having a first flow restrictor in a substantially closed configuration.

FIG. 5 is a perspective view of the valve of FIG. 4 having the first flow restrictor in an open configuration.

FIG. 6 is an alternative perspective view of the valve of FIG. 4.

FIG. 7 is a schematic representation of a valve containing a solenoid.

DETAILED DESCRIPTION

Figure 1:
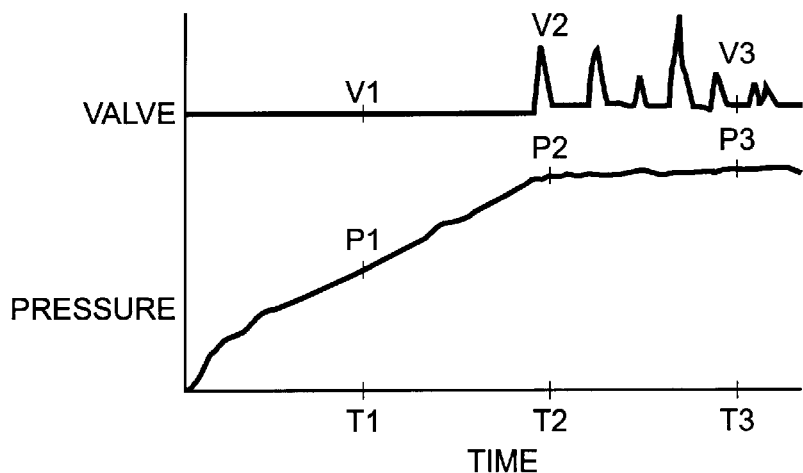
FIG. 1 is a graph of pressure and configuration changes in a prior art valve that does not have a high hysteresis level.

In FIG. 1, pressure and valve configurations of a prior art valve are both graphed as a function of time. The graph shows that such valves do not have a high level of hysteresis. At time 1 (T1), a first pressure (P1) in the valve causes the valve to be closed (V1). At time 2 (T2), a second pressure (P2) is a threshold pressure that opens the valve (V2). Since the valve does not have a high hysteresis level, the valve opens and closes at about the threshold pressure. For example, at time 3 (T3), the valve is at a third pressure (P3), which is about the threshold pressure of P2, however, the valve is closed (V3).

Figure 2:
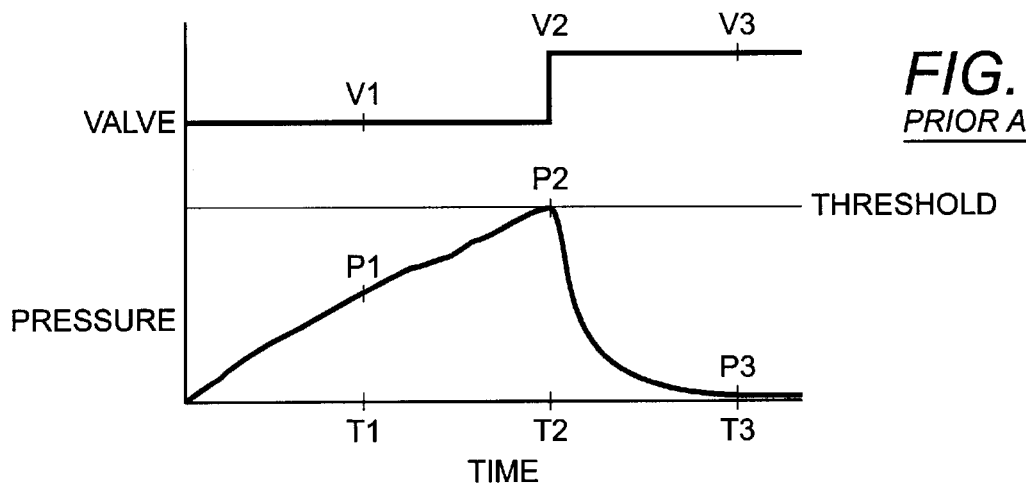
FIG. 2 is a graph of pressure and configuration changes in a prior art valve that opens upon a threshold pressure but does not close when the pressure drops below the threshold pressure.

In FIG. 2, pressure and valve configurations of another prior art valve are both graphed as a function of time. Here, the valve opens at a threshold pressure, but does not close at all, even after the pressure drops to zero. At time 1 (T1), a first pressure (P1) in the valve causes the valve (V1) to be closed. At time 2 (T2), a second pressure (P2) is a threshold pressure that opens the valve (V2). When the pressure drops to a third pressure (P3) at time 3 (T3), the valve remains open (V3). After T3, the valve remains open regardless of pressure change.

Figure 3:
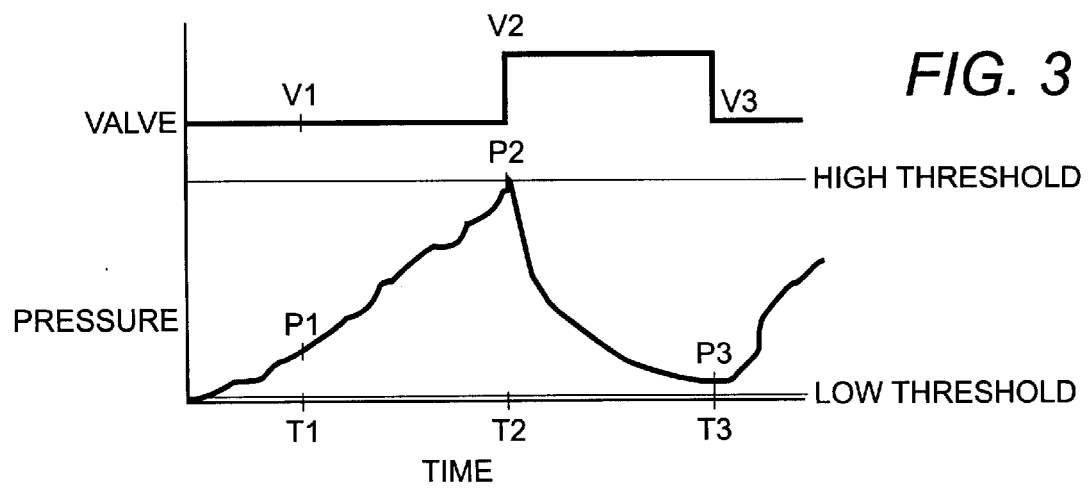
FIG. 3 is a graph of pressure and configuration changes in a valve of the present subject matter that automatically opens upon a threshold pressure, remains open for a period of time regardless of the pressure, and then automatically closes.

In FIG. 3, pressure and valve configurations of a valve according to the inventive subject matter are again graphed as a function of time. Here, the valve opens at a high threshold pressure and remains open until a low threshold pressure is reached. The closing may be triggered by reaching of the low threshold, or passage of a given length of time, or some other factor. The low threshold may or may not be ambient pressure. At time 1 (T1), a first pressure (P1) in the valve causes the valve to be closed (V1). At time 2 (T2), a second pressure (P2) is a threshold pressure that opens the valve (V2). The valve remains open until time 3 (T3) and pressure (P3), at which point it closes (V3).

As used herein, "high threshold pressure" is defined as the pressure above which the valve opens, and "low threshold pressure" is defined as the pressure below which the valve closes. The high threshold pressure is greater than the low threshold pressure, preferably by greater than 5 pounds/square inch (psi), more preferably by greater than 7 psi, and even more preferably by greater than 10 psi. The valve may or may not open due to the high threshold pressure and/or close due to the low threshold pressure. For example, a solenoid may open and close the valve in a time-dependent manner.

In FIG. 4, a valve 10 generally includes a housing 60, a first flow restrictor 30, a magnet 40, a locking device 50, a first opening 20 in the housing 60, and a second opening 70 in the housing 60, all of which cooperate to substantially restrict a fluid flow 90 through a catheter or other tube 80.

The housing 60 can be of any suitable size, shape, color, materials, and so forth. In FIG. 4, the housing is rectangular-shaped and of an appropriate size suitable for containing the valve. It is contemplated that housings can be manufactured to a certain size so as to accommodate an appropriate application. In FIG. 4, the structure of the housing 60 is appropriate for the valve 10 that utilizes the first opening 20 as an entryway for access to the valve 10.

The first flow restrictor 30 can be any mechanical device that transitions between a substantially open configuration and a substantially closed configuration. In FIG. 4, the first flow restrictor 30 comprises the magnet 40 and the locking device 50. The magnet 40 may be of any suitable size and shape that allows attraction of a metallic object for the purpose of closing the valve 10. In FIG. 4, the magnet 40 is shaped as a cylinder and positioned horizontally in the housing 60. A top portion of the magnet 40 is exposed to the inside of the housing 60 and a bottom portion of the magnet 40 is embedded in the housing 60.

The locking device 50 can be any mechanical device that further restricts a fluid flow through a catheter. "Restriction" is herein defined as a decrease in the fluid flow by up to about 20%, preferably by up to about 40%, more preferably by up to about 80%, and even more preferably by up to about 99%. "Fluid" is herein defined as anything that flows, including especially urine, but also other liquids, gases, and flowable particulates such as sand, and graphite.

In FIG. 4, the locking device 50 is a ferrous wire that is positioned in the same 2-dimensional plane as the magnet 40. A stationary end of the locking device 51 is coupled to the housing 60 and the magnet 40, while an opposing end of the locking device 52 is free to rotate towards the length of the magnet 40 or away from the magnet 40 in the same 2-dimensional plane on an axis defined by the stationary end of the locking device 51. Here, the first flow restrictor 30 is in a substantially closed position in which the opposing end of the locking device 52 has rotated toward the length of the magnet 40, thereby positioning the length of the wire parallel and substantially coupled to the length of the magnet 40.

The second opening 70 in the housing 60 can be of any appropriate size and shape to allow the locking device 50 to open and substantially close the valve 10 without obstruction by the housing 60. A housing may be designed without the second opening 70, however, the housing must not obstruct the locking device from transitioning between the open and closed configuration. In FIG. 4, the second opening 70 in the housing 60 is slit-shaped, wherein the length of the slit is in the same 2-dimensional plane as the rotation of the locking device 50 and the width of the slit can accommodate the width of the locking device 50 during the rotation.

The first opening 20 in the housing 60 can be of any appropriate size and shape to allow the catheter 80 to enter the housing 60 and pass through the first flow restrictor 30. In FIG. 4, the first opening 20 is rectangular-shaped and of a sufficient size to accommodate the width of the catheter 80 as it passes through the housing 60 without obstructing the fluid flow 90 inside the catheter 80.

The catheter 80 may be comprised of any flexible material that permits the valve 10 to effectively restrict or allow passage of the fluid flow 90 through the catheter 80, including a rubber tube or a tube comprising any suitable polymer having flexible characteristics. In FIG. 4, the catheter 80 is a solid, flexible tube that passes through the housing 60 and in between the magnet 40 and the locking device 50 while in the housing 60.

The fluid flow 90 passes through the catheter 80 unidirectionally, from the first opening 20 of the housing 60 to a second flow restrictor 100. The fluid may comprise, for example, urine for use in a urinary catheter. To maintain the valve in a substantially closed position in FIG. 4, a first pressure from the fluid flow 90 through the catheter 80 will cause the magnetic force of the magnet 40 to attract the locking device 50 and substantially close the catheter 80, thereby restricting the flow fluid 90.

In FIG. 5, the valve 10 is shown with the first flow restrictor 30 in the open configuration. Here, the opposing end of the locking device 52 is rotated away from the magnet 40, thereby causing the first flow restrictor 30 to have a V-shaped configuration and leaving a space with which the fluid flow 90 may pass through the catheter 80. The first flow restrictor 30 transitions into the open configuration when a threshold pressure in the fluid flow 90 inside the catheter 80 causes the opposing end of the locking device 52 to rotate away from the magnet 40. The force of the threshold pressure must be greater than the attractive force of the magnet 40 toward the locking device 50 to cause the uncoupled end of the locking device 52 to rotate away from the magnet 40.

In FIG. 6, the valve 10 is seen from a perspective that shows a second flow restrictor 100. The second flow restrictor 100 may be of any suitable size and shape that will limit the amount of the fluid flow 90 subsequent to exposure to the first flow restrictor 30. If the valve 10 is closed, there is an insufficient volume of the fluid flow 90 to activate the restriction function of the second flow restrictor 100. If the valve 10 is open, there will be sufficient fluid flow 90 exiting from the first flow restrictor 30 to activate the restriction function of the second flow restrictor 100 and cause a decrease in the fluid flow 90. In FIG. 6, the second flow restrictor 100 is an opening in the housing 60 that further restricts the fluid flow 90 in the catheter 80. The second flow restrictor may be an opening in a housing of any suitable size and shape to cause a fixed reduction in fluid flow, depending on the size and shape of the opening. Alternatively, the second flow restrictor may be a separate structure, apart from the housing that contains the locking device and downstream with respect to the fluid flow.

In FIG. 7, an electronically-operated controller 200, comprises a battery 210, a valve 220, a connector 230, a first flow restrictor 240 all acting in cooperation in controlling a fluid flow 90 in a catheter 80.

The battery 210 can be any device that provides an electric potential for providing electrical energy.

The valve 220 may be used to control the fluid flow 90 in a time-dependent, a flow-dependent, or a pressure-dependent manner.

The connector 230 can be any device suitable for transmitting an electronic signal from the solenoid 220 to the first flow restrictor 240. Suitable materials include wires and other electronic transmitting conduits.

The first flow restrictor 240 can be any device suitable for receiving an electronic signal from connector 230 to externally restrict the catheter 80 and thereby restrict the fluid flow 90 contained in the catheter 80.

The automatic valve of the present invention may have various applications, especially where high hysteresis is desired. As used herein the term "hysteresis" refers to a delay in the closing of the valve due to the weaker force of the closing mechanism when the valve is open than when the valve is closed. As discussed above, this combination of features is especially desirable for use with urinary catheters. A urinary catheter according to the inventive subject matter is advantageous because the valve portion is positioned outside of the catheter, and can easily be autoclaved and reused with a new catheter. Since the fluid never contacts the valve, the valve can be quite durable, and therefore, not require frequent replacement.

Thus, specific embodiments and applications of high hysteresis valves have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A valve operable upon a flexible tube defining a lumen, comprising:
    a first flow restrictor positioned outside of the lumen, which transitions between an open configuration and a closed configuration;
    a closing mechanism that automatically positions the first flow restrictor to the closed configuration when a pressure in a fluid within the lumen is below a low threshold pressure; and
    an opening mechanism that automatically positions the first flow restrictor to the open configuration when the pressure in the fluid within the lumen is above a high threshold pressure that is higher than the low threshold pressure.

2. The valve of claim 1 wherein the first flow restrictor is positioned outside the tube.

3. The valve of claim 1 wherein the fluid flows within the lumen to define an upstream and a downstream, and further comprising a second flow restrictor downstream of the first flow restrictor.

4. The valve of claim 3 wherein the first flow restrictor and the second flow restrictor are contained within a single housing.

5. The valve of claim 1 wherein the closing mechanism comprises a magnet.

6. The valve of claim 1 wherein the closing mechanism comprises a solenoid.

7. The valve of claim 6 wherein the solenoid closes the valve in a time-dependent manner.

8. The valve of claim 6 wherein the solenoid closes the valve in a flow-dependent manner.

9. The valve of claim 6 wherein the solenoid closes the valve in a pressure dependent manner.

10. A drainage system comprising the valve of claim 1, wherein the tube is a catheter.

11. The drainage system of claim 10 wherein the catheter comprises a urinary catheter.

* * * * *